(12) United States Patent
Kim et al.

(10) Patent No.: US 11,804,298 B2
(45) Date of Patent: Oct. 31, 2023

(54) CANCER DIAGNOSTIC APPARATUS AND CANCER DIAGNOSTIC SYSTEM USING THE SAME

(71) Applicants: Joon Kim, Seoul (KR); Il Wong Kim, Gyeonggi-do (KR)

(72) Inventors: Joon Kim, Seoul (KR); Il Wong Kim, Gyeonggi-do (KR)

(73) Assignees: Joon Kim, Seoul (KR); Il Wong Kim, Gyeonggi-do (KR)

(*) Notice: Subject to any disclaimer, the term of this patent is extended or adjusted under 35 U.S.C. 154(b) by 1506 days.

(21) Appl. No.: 16/037,503

(22) Filed: Jul. 17, 2018

(65) Prior Publication Data

US 2019/0017104 A1    Jan. 17, 2019

(30) Foreign Application Priority Data

Jul. 17, 2017 (KR) .................. 10-2017-0090479
Aug. 8, 2017 (KR) .................. 10-2017-0100333

(51) Int. Cl.

| | | |
|---|---|---|
| G16H 40/67 | (2018.01) | |
| C12Q 1/6825 | (2018.01) | |
| G01N 33/574 | (2006.01) | |
| G16H 50/20 | (2018.01) | |
| G01N 33/543 | (2006.01) | |
| G06V 10/56 | (2022.01) | |
| G06V 10/143 | (2022.01) | |
| G16H 10/40 | (2018.01) | |
| G01N 35/00 | (2006.01) | |
| G01N 33/536 | (2006.01) | |
| G01N 33/533 | (2006.01) | |

(52) U.S. Cl.
CPC ........... *G16H 40/67* (2018.01); *C12Q 1/6825* (2013.01); *G01N 33/54366* (2013.01); *G01N 33/57488* (2013.01); *G06V 10/143* (2022.01); *G06V 10/56* (2022.01); *G16H 50/20* (2018.01); *G01N 33/533* (2013.01); *G01N 33/536* (2013.01); *G01N 2035/00158* (2013.01); *G06V 2201/03* (2022.01); *G16H 10/40* (2018.01)

(58) Field of Classification Search
CPC ........ G16H 40/67; G16H 50/20; G06V 10/56; G06V 10/143; C12Q 1/6825; G01N 33/54366; G01N 33/57488
See application file for complete search history.

(56) References Cited

U.S. PATENT DOCUMENTS

| | | | |
|---|---|---|---|
| 2007/0054271 A1 | 3/2007 | Polyak et al. | |
| 2012/0308437 A1 | 12/2012 | Zhou et al. | |
| 2017/0023577 A1 | 1/2017 | Mulligan et al. | |
| 2018/0356405 A1* | 12/2018 | Chou ................ | G01N 21/6452 |

FOREIGN PATENT DOCUMENTS

| | | |
|---|---|---|
| JP | 2015-057600 | 3/2015 |
| JP | 2016-048232 | 4/2016 |
| KR | 10-2003-0032809 | 4/2003 |
| KR | 20030037856 | 5/2003 |
| KR | 10-2012-0098992 | 9/2012 |
| KR | 1020130081044 | 7/2013 |
| KR | 10-2013-0138506 | 12/2013 |
| KR | 10-2016-0050414 | 5/2016 |
| KR | 1020160050414 | 5/2016 |
| KR | 10-1705185 | 2/2017 |

OTHER PUBLICATIONS

Kim, Y. et al, Ribosomal protein S3 is secreted as a homodimer in cancer cells, Biochemical and Biophysical Research Communications, 2013, pp. 805-808, vol. 441.

Zong, C. et al, Chemiluminescence Imaging Immunoassay of Multiple Tumor Markers for Cancer Screening, Analytical Chemistry, 2012, pp. 2410-2415, vol. 84, American Chemical Society.

Trnavsky, M. et al, Surface plasmon-coupled emission for applications in biomedical diagnostics, Dublin City University for the Degree of Doctor of Philosophy, Jul. 2009, pp. 1-117.

Thiha, A. et al, A Colorimetric Enzyme-Linked Immunosorbent Assay (ELISA) Detection Platform for a Point-of-Care Dengue Detection System on a Lab-on-Compact-Disc, Sensors, 2015, pp. 11431-11441, vol. 15.

(Continued)

*Primary Examiner* — Jerry Lin
(74) *Attorney, Agent, or Firm* — IP & T GROUP LLP

(57) ABSTRACT

The present invention relates to a cancer diagnostic apparatus for checking a cancer incidence by allowing an antibody (captured antibody), which reacts with an rpS3 (ribosomal protein S3; antigen) capable of checking a phenomenon of a cancer, to react with the rpS3, and performing concentration measurement after extracting an emission signal of the reacted antigen (rpS3), and a cancer diagnostic system using the cancer diagnostic apparatus. The cancer diagnostic system includes: the cancer diagnostic apparatus for irradiating an ultraviolet ray (UV) from a bottom of a bio-chip provided with an antibody reacting with an antigen (ribosomal protein S3; rpS3), making an image from a visible ray obtained from the ultraviolet ray, which is converted by the antigen and the antibody bound to each other while passing through the bio-chip, and extracting only a specific frequency color from the visible ray to generate cancer diagnosis information; and a user terminal.

6 Claims, 13 Drawing Sheets

(56) References Cited

OTHER PUBLICATIONS

Sanjay, S. T. et al, Biomarker detection for disease diagnosis using cost-effective microfluidic platforms, Analyst (2015), pp. 7062-7081, vol. 140, No. 21, The Royal Society of Chemistry.
Notice of Allowance issued by the Korean Intellectual Property Office dated Jun. 28, 2019.
Minoo Askari et al., Application of an Antibody Biochip for p53 Detection and Cancer Diagnosis, 2001 American Chemical Society and American Institute of Chemical Engineers, Biotechnol. Prog. 2001, vol. 17, No. 3, Apr. 11, 2001, pp. 543-552.
Office Action issued by the Korean Intellectual Property Office dated Nov. 14, 2018.

* cited by examiner

CANCER DIAGNOSTIC APPARATUS AND CANCER DIAGNOSTIC SYSTEM USING THE SAME

CROSS-REFERENCES TO RELATED APPLICATION

The present application claims priority under 35 U.S.C. § 119(a) to Korean application number 10-2017-0090479, filed on Jul. 17, 2017 and Korean application number 10-2017-0100333, filed on Aug. 8, 2017, in the Korean Intellectual Property Office, which is incorporated herein by reference in its entirety.

BACKGROUND OF THE INVENTION

1. Field of the Invention

The present invention relates to a cancer diagnostic apparatus and a cancer diagnostic system using the same, and more particularly, to a cancer diagnostic apparatus for checking a cancer incidence by allowing an antibody (captured antibody), which reacts with an rpS3 (ribosomal protein S3; antigen) capable of checking a phenomenon of a cancer, to react with the rpS3, and performing concentration measurement after extracting an emission signal of the reacted antigen (rpS3), and a cancer diagnostic system using the cancer diagnostic apparatus.

2. Description of the Related Art

Proteins are involved in every physiological process, from cell signaling to tissue rearrangement for an organ action. Thus, protein synthesis is a very important process in a cell, and ribosomes have a function of synthesizing proteins. Ribosomes are organelles which serve to synthesize proteins by linking amino acids, and are composed of a massive complex formed by binding many ribosomal proteins and ribosomal RNAs.

A ribosomal protein S3 (rpS3) is a component of the ribosome, and is located on an outer surface of a 40S subunit while being cross-linked to initiation factors eIF2 and eIF3. The rpS3 has a nuclear localization signal at an N-terminal site, which means that rpS3 has a function in cytoplasm and a repair function in a nucleus. In addition, many ribosomal proteins have a second function such as replication, transcription, RNA processing, DNA repair, and malignant transformation.

An rpS3 gene is located at 11q13.3-q13.5 on a human chromosome 11. Of particular note is that the rpS3 gene is reported to be overexpressed in patients having a colorectal cancer. Thus, gene products of the rpS3 are absent or modified in XP-D and overexpressed in the colorectal cancer, and there is high possibility that the gene products may be associated with other cancers. In addition, in a research on an 11q13.3-q13.5 site, it is known that structural abnormality and amplification of genes frequently occur and the gene products are overexpressed in an incidence of a human cancer such as a multiple endocrine neoplasia type, a breast carcinoma and a B-cell neoplasm (Pogue-Geile et al., Mol. Cell. Biol., 11: 3842-3849, 1991).

Over the past several years, an intensive research has been conducted on causes, diagnostic schemes, and treatment schemes of the cancer. However, no definitive treatment has yet been developed to effectively treat the cancer. Therefore, the most effective scheme is to detect the cancer at an incipient stage to remove cancer cells or inhibit growth of the cancer cells by a surgical operation or medication.

In general, cancers cause symptoms such as involvement in surrounding tissues or lymph node metastasis due to the growth of the cancer cells. However, in the incipient stage, cancers frequently progress without any subjective symptoms, so that the cancers are frequently found only after they have metastasized to other organs.

Therefore, an early diagnosis is required to reduce mortality from the cancers. Generally, cancers are confirmed by diagnoses using ultrasound, CT using X-rays, MRI or the like, and finally confirmed through a biopsy. Since there is inconvenience that patients suffer from pain during schemes such as the biopsy, it is necessary to develop an examination scheme capable of diagnosing the cancer more easily and rapidly.

Many cellular proteins appear to increase or decrease in various body fluids of patients having cancers. In cancer patients, a scheme of detecting a cancer-specific antigen by analyzing presence or an expression level of a protein representing a cancer cell-specific expression pattern can be used for a cancer diagnosis or prediction of a cancer stage.

<Patent document 1> to <Patent document 3> disclose techniques which have been proposed for the cancer diagnosis or the cancer stage prediction.

In the related art disclosed in <Patent document 1>, the cancer is diagnosed by using a polyclonal antibody (S3CA) which can be usefully used to diagnose leukemia or various cancers by specifically recognizing sequences 164 to 243 of the amino acids in the rpS3.

In addition, in the related art disclosed in <Patent document 2>, a chaperoning composition for a protein including, as an active ingredient, one protein selected from the group consisting of ribosomal proteins RPS3a, RPL27a, RPS24, RPL8, RPL35a, and RPS27a is provided for diagnosing a liver cancer. It is preferable that the RPS3a has an amino acid sequence designated by a sequence number 1, the RPL27a has an amino acid sequence designated by a sequence number 2, the RPS24 has an amino acid sequence designated by a sequence number 3, the RPL8 has an amino acid sequence designated by a sequence number 4, the RPL35a has an amino acid sequence designated by a sequence number 5, and the RPS27a has an amino acid sequence designated by a sequence number 6.

In addition, the related art disclosed in <Patent document 3> provides a method for diagnosing a cancer or predicting a cancer stage by using a ribosomal protein S3 (rpS3) which is expressed in cancer cells and secreted out of the cells. Measuring an amount of the rpS3 secreted out of the cells is a rapid and convenient scheme using cell secretions such as blood, and is very useful for the cancer diagnosis or the cancer stage prediction.

DOCUMENTS OF RELATED ART

Patent Documents (Patent document 1) Korean Patent Application Publication No. 2003-0037856 (published on May 16, 2003, and titled "Polyclonal antibody to ribosomal protein S3 and cancer diagnostic kit using the same")
(Patent document 2) Korean Patent Application Publication No. 10-2013-0081044 (published on Jul. 16, 2013, and titled "Chaperoning composition and composition for diagnosing liver cancer including ribosomal protein S3 as active ingredient")

(Patent document 3) Korean Patent Application Publication No. 10-2016-0050414 (published on May 11, 2016, and titled "Method for diagnosing cancer by using ribosomal protein S3")

SUMMARY OF THE INVENTION

However, while the above general cancer diagnosis techniques and related arts are utilized for the cancer diagnosis using the ribosomal protein S3, it is difficult for a general user to use the above techniques and related arts for self-diagnosing a cancer.

Accordingly, the present invention has been proposed to solve the above problems occurring in the related art, and an object of the present invention is to provide a cancer diagnostic apparatus for checking a cancer incidence by allowing an antibody (captured antibody), which reacts with an rpS3 (ribosomal protein S3; antigen) capable of checking a phenomenon of a cancer, to react with the rpS3, and performing concentration measurement after extracting an emission signal of the reacted antigen (rpS3), and a cancer diagnostic system using the cancer diagnostic apparatus.

Another object of the present invention is to provide a cancer diagnostic apparatus which allows a general user to simply check a cancer incidence through a self-diagnosis, and a cancer diagnostic system using the cancer diagnostic apparatus.

To achieve the objects described above, according to the present invention, there is provided a cancer diagnostic apparatus including: a power supply unit for supplying a power; a bio-chip provided at an upper portion thereof with an antibody reacting with an antigen (ribosomal protein S3; rpS3); an ultraviolet diode for irradiating an ultraviolet ray (UV) from a bottom of the bio-chip; a sensor for making an image from a visible ray obtained from the ultraviolet ray, which is converted by the antigen and the antibody bound to each other while passing through the bio-chip; a central processing unit (CPU) for extracting only a specific frequency color for a cancer diagnosis from image information outputted from the sensor as a combine ratio coefficient to generate cancer diagnosis information from a pre-set graph of an antibody-and-antigen combine ratio based on the extracted combine ratio coefficient; and a communication unit for converting the cancer diagnosis information generated by the CPU into wireless communication format data to transmit the converted wireless communication format data.

In detail, the sensor may include: a camera lens for focusing the visible ray obtained from the ultraviolet ray, which is irradiated upward from the bottom of the bio-chip and converted by the antigen and the antibody bound to each other while passing through the bio-chip, to photograph the visible ray; and an image sensor for photographing the visible ray focused by the camera lens to make the image.

In detail, the CPU may compare the combine ratio coefficient with the pre-set graph of the antibody-and-antigen combine ratio to generate the cancer diagnosis information after the antibody and the antigen are completely bound to each other.

To achieve the objects described above, according to the present invention, there is provided a cancer diagnostic system using a cancer diagnostic apparatus, the cancer diagnostic system including: the cancer diagnostic apparatus for irradiating an ultraviolet ray (UV) from a bottom of a bio-chip provided with an antibody reacting with an antigen (ribosomal protein S3; rpS3), making an image from a visible ray obtained from the ultraviolet ray, which is converted by the antigen and the antibody bound to each other while passing through the bio-chip, and extracting only a specific frequency color from the visible ray to generate cancer diagnosis information; and a user terminal for acquiring the cancer diagnosis information generated by the cancer diagnostic apparatus through a cancer diagnostic application to transmit the acquired cancer diagnosis information to a cancer diagnostic server, and displaying cancer diagnosis result information, which is a result of analysis performed by the cancer diagnostic server, on a screen.

In detail, the cancer diagnostic apparatus may include: a power supply unit for supplying a power; a bio-chip provided at an upper portion thereof with the antibody reacting with the antigen (ribosomal protein S3; rpS3); an ultraviolet diode for irradiating the ultraviolet ray (UV) from the bottom of the bio-chip; a sensor for making the image from the visible ray obtained from the ultraviolet ray, which is converted by the antigen and the antibody bound to each other while passing through the bio-chip; a central processing unit (CPU) for extracting only the specific frequency color for a cancer diagnosis from image information outputted from the sensor as a combine ratio coefficient to generate the cancer diagnosis information from a pre-set graph of an antibody-and-antigen combine ratio based on the extracted combine ratio coefficient; and a communication unit for converting the cancer diagnosis information generated by the CPU into wireless communication format data to transmit the converted wireless communication format data.

In detail, the sensor may include: a camera lens for focusing the visible ray obtained from the ultraviolet ray, which is irradiated upward from the bottom of the bio-chip and converted by the antigen and the antibody bound to each other while passing through the bio-chip, to photograph the visible ray; and an image sensor for photographing the visible ray focused by the camera lens to make the image.

In detail, the CPU may compare the combine ratio coefficient with the pre-set graph of the antibody-and-antigen combine ratio to generate the cancer diagnosis information after the antibody and the antigen are completely bound to each other.

In detail, the user terminal may be implemented as a mobile device capable of performing short-range wireless communication with the cancer diagnostic apparatus and capable of performing data communication with the cancer diagnostic server through a network, and the mobile device may be one of a smart phone, a personal digital assistant (PDA), and a smart pad.

In detail, the user terminal may include: a communication module for transmitting and receiving cancer diagnosis-related data to and from the cancer diagnostic apparatus and the cancer diagnostic server; a cancer diagnostic application execution unit for storing and executing the cancer diagnostic application; a cancer diagnosis control unit for controlling the execution of the cancer diagnostic application, transmitting the cancer diagnosis information received from the cancer diagnostic apparatus to the cancer diagnostic server to request analysis, and controlling storage and display of the cancer diagnosis result information received from the cancer diagnostic server; and a display unit for displaying the cancer diagnosis result information, which is generated from the cancer diagnosis control unit, on the screen.

In detail, the cancer diagnostic server may diagnose a cancer incidence by comparing an rpS3 concentration included in the cancer diagnosis information with reference cancer determination data preset based on big data.

According to the present invention, the cancer incidence is simply checked by allowing the antibody (captured antibody), which reacts with the rpS3 (ribosomal protein S3; antigen) capable of checking the phenomenon of the cancer, to react with the rpS3, and performing the concentration measurement after extracting the emission signal of the reacted antigen (rpS3).

In addition, according to the present invention, a general user can simply check the cancer incidence through the self-diagnosis.

DETAILED DESCRIPTION OF THE INVENTION

Hereinafter, a cancer diagnostic apparatus and a cancer diagnostic system using the same according to a preferred embodiment of the present invention will be described in detail with reference to the accompanying drawings.

Embodiment 1

Figure 1:
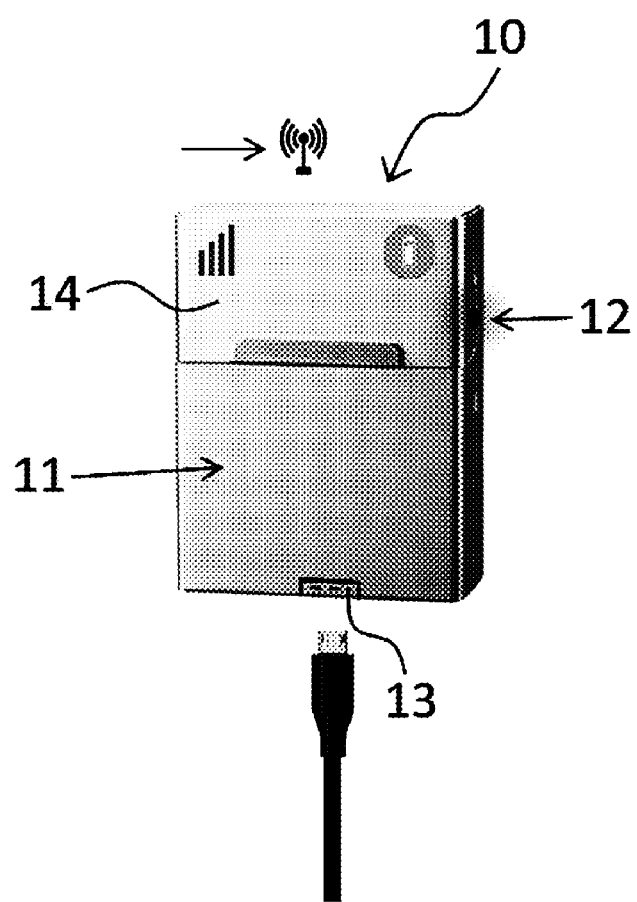
FIG. 1 is a perspective view showing an embodiment of a cancer diagnostic apparatus according to the present invention.

FIG. 1 is a view showing an external appearance of a cancer diagnostic apparatus 10 according to a preferred embodiment of the present invention, and the cancer diagnostic apparatus 10 includes a body 14, a cover 11, a power switch 12, and a charging port 13.

The cover 11 may be an open-close type cover, and the cover 11 is opened during a cancer diagnosis to drip blood at a predetermined position of the bio-chip 16 mounted inside the body 14. When the cancer diagnostic apparatus 10 is not in use, the cover 11 is closed to prevent foreign substances or the like from being introduced into the body 14.

In this case, the cover 11 has been described as an open-close type cover, but the present invention is not limited thereto, and it is also possible to replace the cover with a sliding door.

The charging port 13 may be various charging ports, and it is assumed that the charging port 13 is implemented as a USB charging port according to the embodiment of the present invention.

Figure 2:
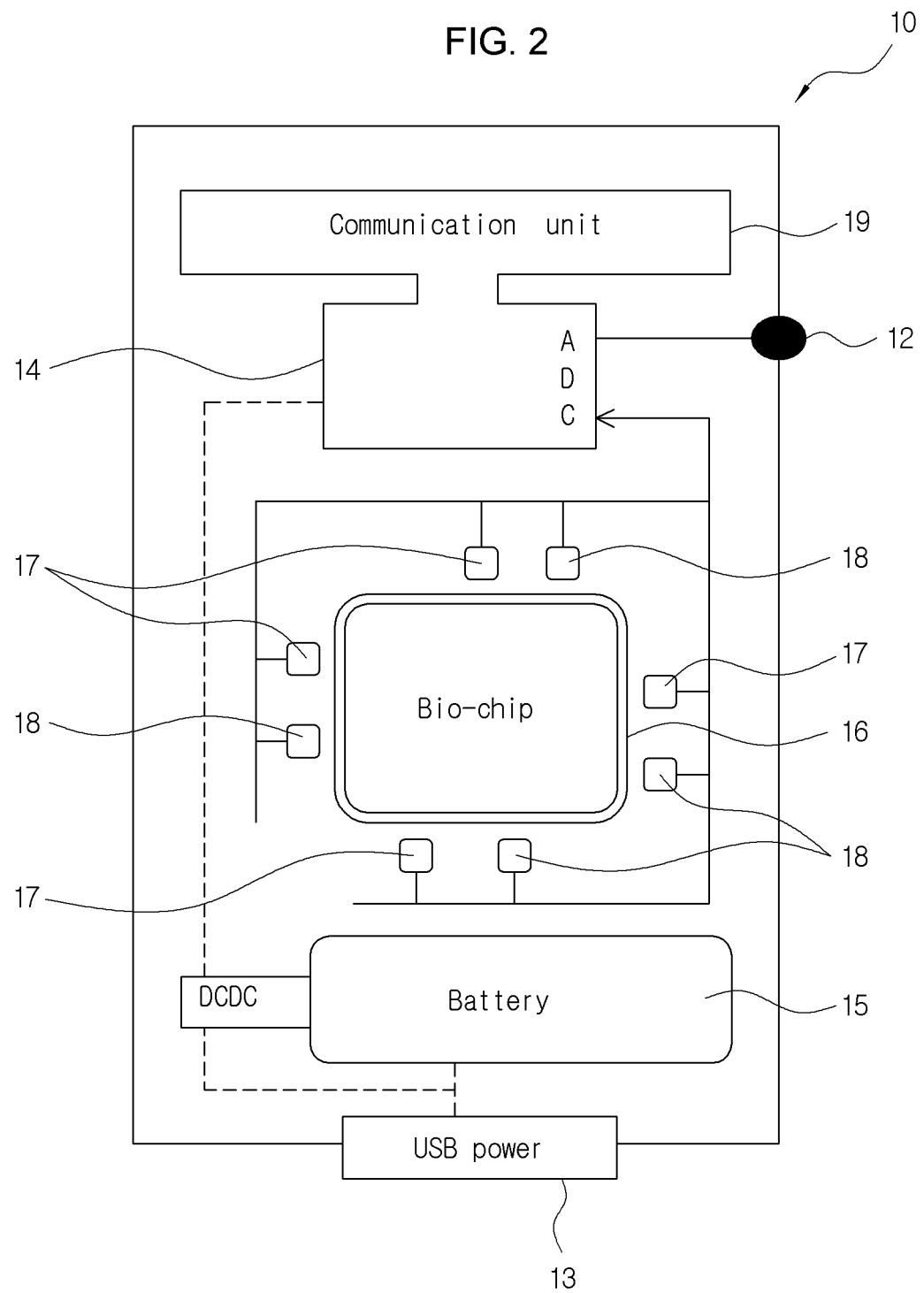
FIG. 2 is a view showing a detailed configuration of the cancer diagnostic apparatus of FIG. 1.

FIG. 2 is a view showing the embodiment of the cancer diagnostic apparatus 10 including: a power supply unit 15 for supplying a power; a bio-chip 16 provided at an upper portion thereof with an antibody (captured antibody) reacting with an antigen (ribosomal protein S3; rpS3); an ultraviolet diode 17 for irradiating an ultraviolet ray (UV) from a bottom of the bio-chip 16; a sensor 18 for making an image from a visible ray obtained from the ultraviolet ray, which is converted by the antigen and the antibody bound to each other while passing through the bio-chip 16; a central processing unit (CPU) 19 for extracting only a specific frequency color for a cancer diagnosis from image information outputted from the sensor 18 as a combine ratio coefficient to generate cancer diagnosis information from a pre-set graph of an antibody-and-antigen combine ratio based on the extracted combine ratio coefficient; and a communication unit 19a for converting the cancer diagnosis information generated by the CPU 19 into wireless communication format data to transmit the converted wireless communication format data.

In this case, the sensor 18 may include: a camera lens 18a for focusing the visible ray obtained from the ultraviolet ray, which is irradiated upward from the bottom of the bio-chip 16 and converted by the antigen and the antibody bound to each other while passing through the bio-chip 16, to photograph the visible ray; and an image sensor 18b for photographing the visible ray focused by the camera lens 18a to make the image.

The CPU preferably compares the combine ratio coefficient with the pre-set graph of the antibody-and-antigen combine ratio to generate the cancer diagnosis information after the antibody and the antigen are completely bound to each other.

Hereinafter, the operation of the cancer diagnostic apparatus (kit), which has a configuration as described above, will be described in detail.

A user operates the power switch 12 of the cancer diagnostic apparatus 10 to an ON state in order to check the cancer incidence or a cancer stage of the user. When the power switch 12 is operated to the ON state, the power charged by a battery 15 is supplied to a driving power supply.

When the power is supplied, the CPU 19 performs a cancer diagnosis process according to a predetermined process.

To this end, the user opens the cover 11 and drips the blood for the cancer diagnosis at the upper portion of the bio-chip 16 after the cancer diagnostic apparatus 10 is supplied with the power.

Figure 3A:
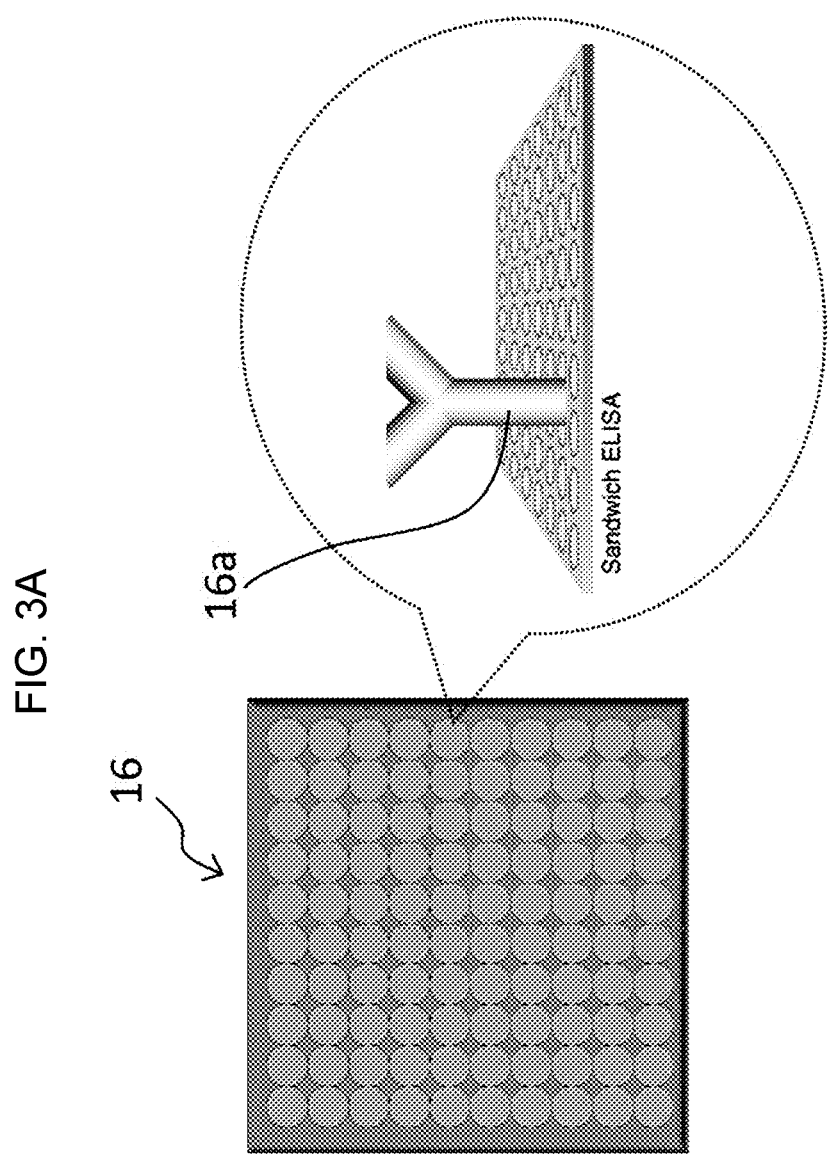
FIGS. 3A and 3B are views showing the configuration of a bio-chip.
Figure 3B:
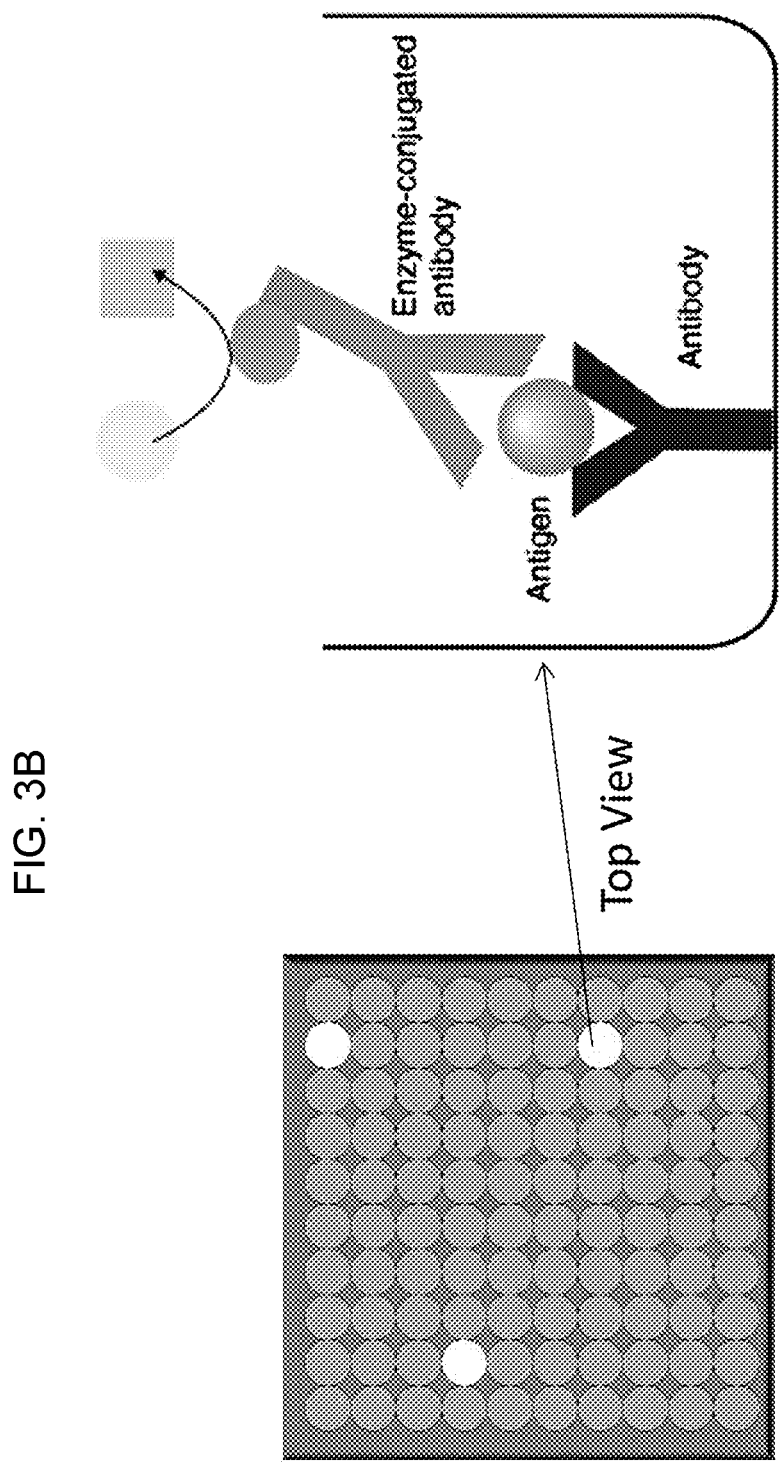

In this case, as shown in FIGS. 3A and 3B, the bio-chip 16 is provided at the upper surface thereof with an antibody (captured antibody) 16a reacting with the rpS3, which is an antigen 16b for cancer expression.

Figure 4:
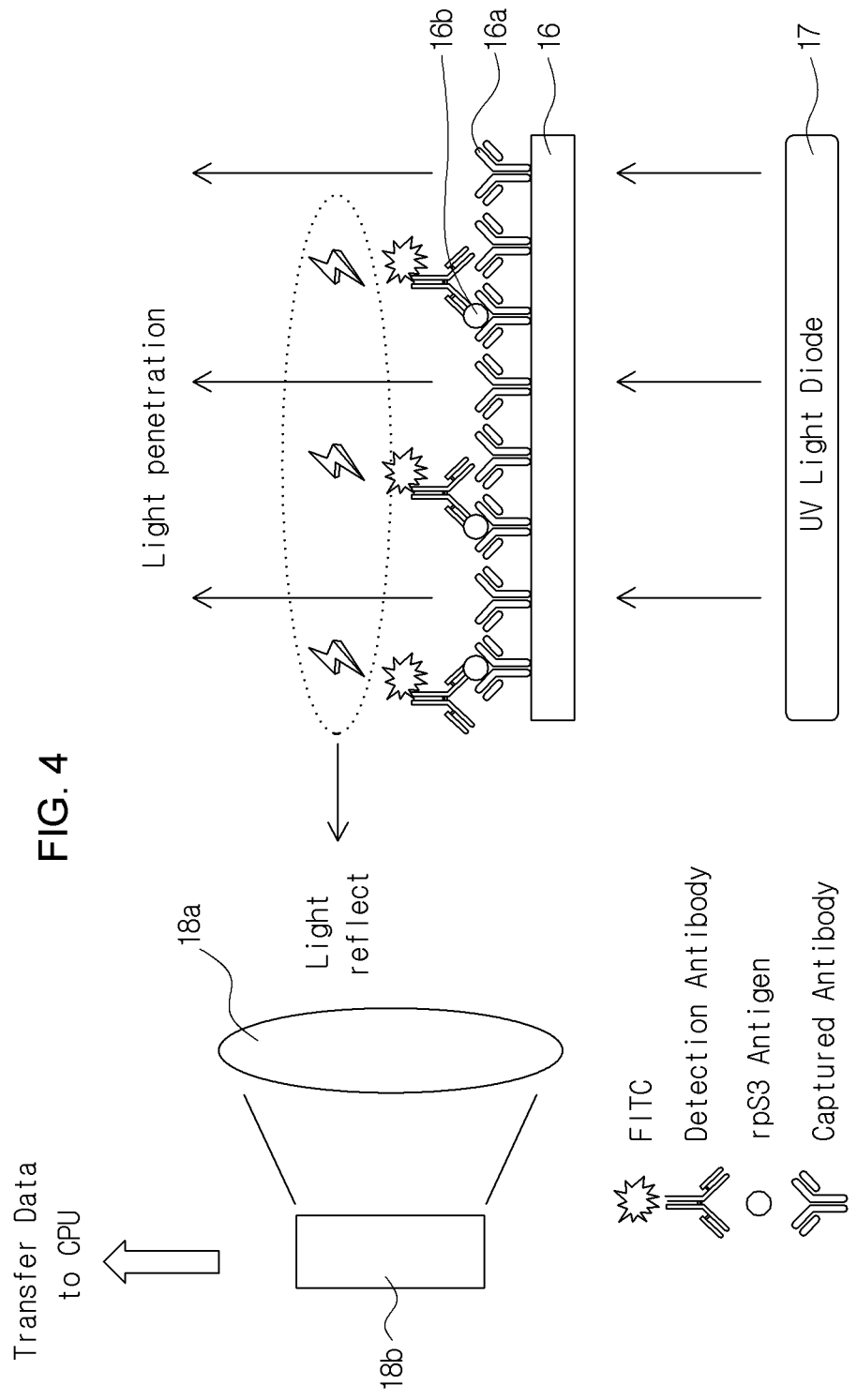
FIG. 4 is a schematic view for explaining generation of cancer diagnosis information in the cancer diagnostic apparatus.

As shown in FIG. 4, the antigen 16a contained in the blood is bound to the antibody 16a, and then a binding strength between the antigen 16a and the antibody 16a is increased by a protective antibody 16c.

At this time, under the control of the CPU 19, the ultraviolet ray is irradiated to the bio-chip 16 by the ultraviolet diode 17 located under or at a side of the bio-chip 16.

Next, the sensor 18 makes an image from the visible ray obtained from the ultraviolet ray while passing through the bio-chip 16.

For example, the camera lens 18a of the sensor 18 focuses the visible ray obtained from the ultraviolet ray, which is irradiated upward from the bottom of the bio-chip 16 and converted into the visible ray (fluorescent light) by the antigen and the antibody bound to each other while passing through the bio-chip 16, to photograph the visible ray, and the image sensor 18b photographs the visible ray focused by the camera lens 18a to make the image.

In this case, it is preferable that the bio-chip 16 is detachably coupled to the body 14, provided with an antibody corresponding to an antigen of a specific cancer to diagnose the specific cancer, and provided for a single use. Therefore, when cancer diagnosis information for diagnosing the specific cancer is generated, the used bio-chip is separated from the body 14, discarded, and replaced with another bio-chip including the antibody.

As a result, the visible ray obtained from the irradiated ultraviolet ray varies depending on the antigen and the antibody bound to each other, and is related to an rpS3 concentration.

Figure 11:
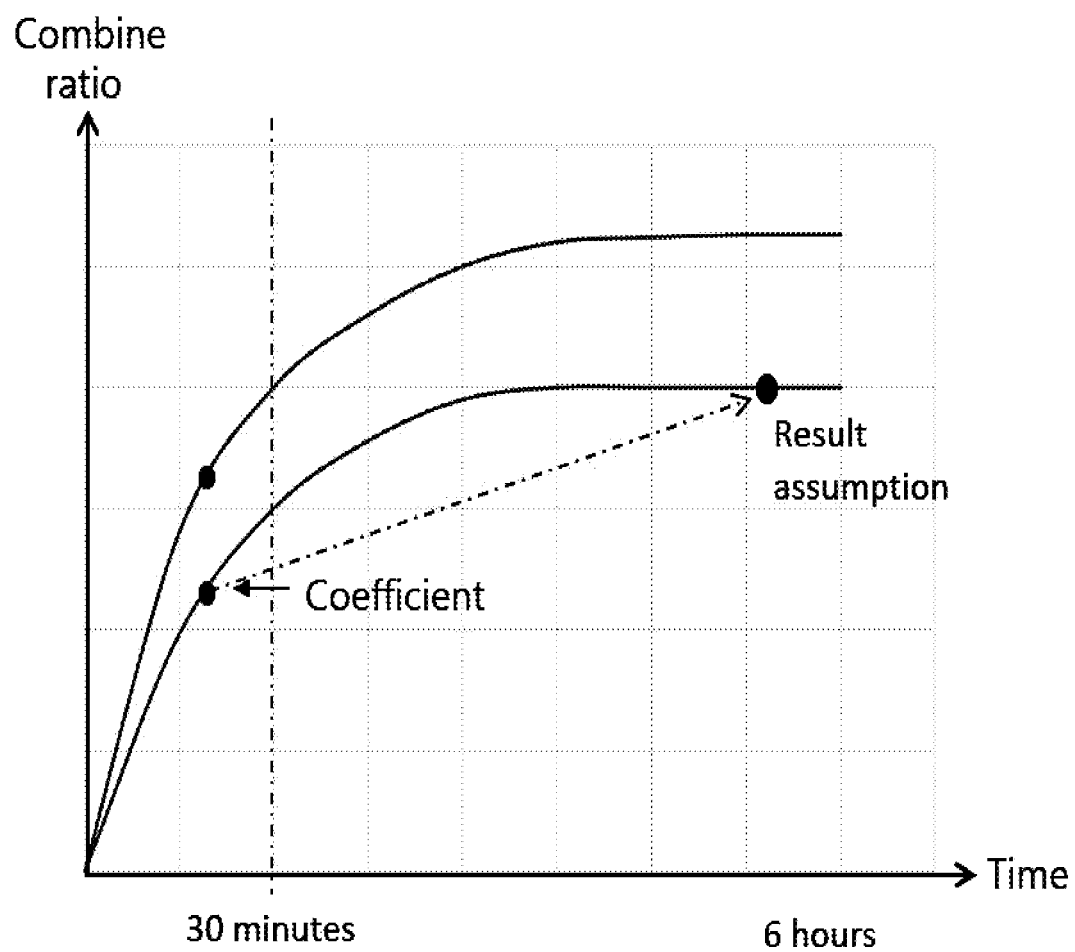
FIG. 11 is a graph of an antibody-and-antigen combine ratio, which is applied to the present invention.
Figure 12:
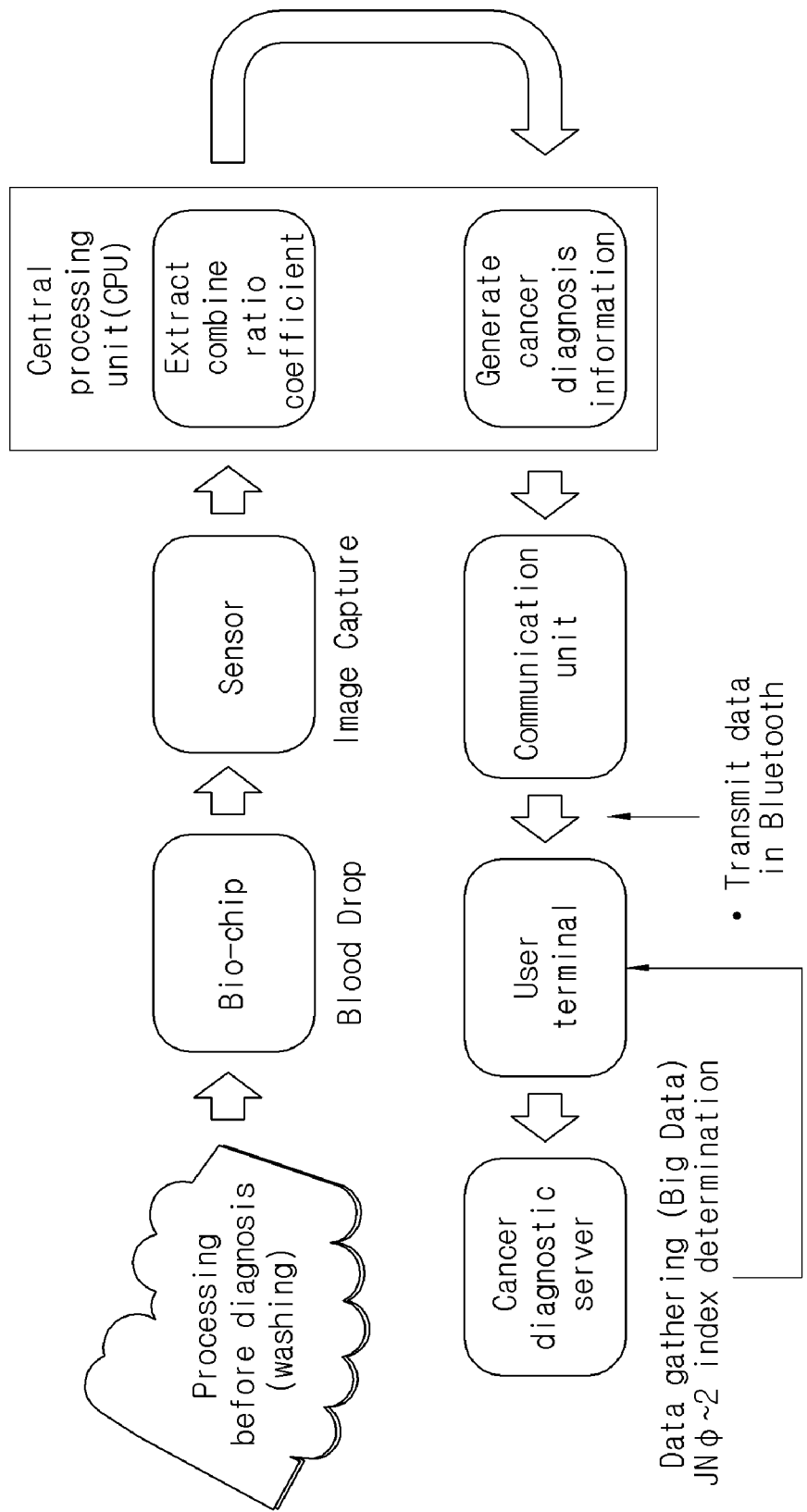
FIG. 12 is a view for explaining a process of diagnosing a cancer by using the cancer diagnostic apparatus according to the present invention.

The CPU 19 extracts only the specific frequency color (for example, a frequency corresponding to green of the rpS3 in CbCr among YCbCr) for the cancer diagnosis from image information (visible ray) outputted from the sensor 18 as a combine ratio coefficient. Next, the CPU 19 generates the cancer diagnosis information by extracting a combine ratio at a time when the antibody and the antigen are completely bound to each other from a pre-set graph of an antibody-and-antigen combine ratio as shown in FIG. 11 based on the extracted combine ratio coefficient, and quantifying the extracted combine ratio into a percentage.

In practice, it takes more than 6 hours to check a normal operation after dropping the blood to an Elisa-LOC, which is a bio-chip. However, it is confirmed through a plurality of experiments that more than 90% of antibodies and antigens are bound to each other 10 minutes after the blood is dropped on the bio-chip. Therefore, on the assumption that the combine ratio is constant, a combine result after 5 hours to 6 hours can be assumed through a statistical graph as shown in FIG. 11 by calculating a coefficient of a function (hyperbolic function) after 5 minutes.

As a result, the above experiment result has an excellent effect that the user can shorten a time required for the cancer diagnosis, which is generally 6 hours, to 10 minutes. The cancer diagnosis information generated from the CPU 19 is transmitted to the communication unit 19a, and the communication unit 19a converts the received cancer diagnosis information into wireless communication format data which conforms to a wireless communication scheme to transmit the wireless communication format data. In practice, the cancer diagnosis information received from the cancer diagnostic apparatus 10 is preferably transmitted to the user terminal carried by the user.

The wireless communication scheme is preferably a short-range wireless communication scheme such as Bluetooth, Wi-Fi, and NFC.

As described above, according to the present invention, the cancer diagnostic apparatus may generate the cancer diagnosis information by measuring the specific frequency of the rpS3, so that a general user who does not have medical expertise can use the cancer diagnostic apparatus for self-diagnosing a cancer.

Embodiment 2

<Embodiment 1> relates to the cancer diagnostic apparatus for generating the cancer diagnosis information to allow the user to perform the cancer diagnosis, and <Embodiment 2> relates to a cancer diagnostic system for checking an actual cancer expression by analyzing the cancer diagnosis information acquired from the cancer diagnostic apparatus.

Figure 5:
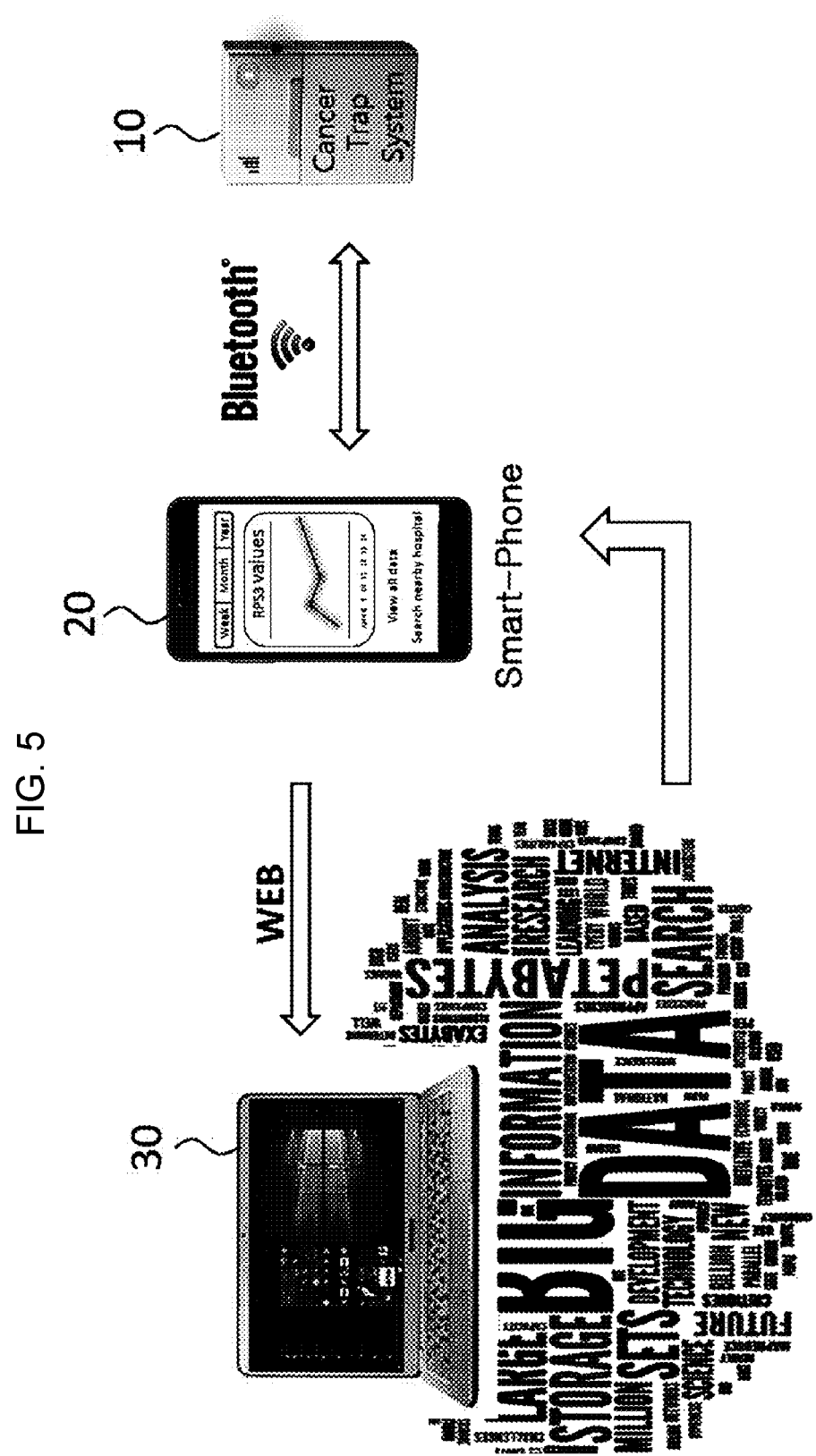
FIG. 5 is a schematic view showing a cancer diagnostic system using the cancer diagnostic apparatus according to the present invention.

FIG. 5 shows the cancer diagnostic system using the cancer diagnostic apparatus according to the present invention, and the cancer diagnostic system includes: the cancer diagnostic apparatus 10 for irradiating an ultraviolet ray (UV) from a bottom of a bio-chip 16 provided with an antibody reacting with an antigen (ribosomal protein S3; rpS3), making an image from a visible ray obtained from the ultraviolet ray, which is converted by the antigen and the antibody bound to each other while passing through the bio-chip 16, and extracting only a specific frequency color from the visible ray to generate cancer diagnosis information; and a user terminal 20 for acquiring the cancer diagnosis information generated by the cancer diagnostic apparatus 10 through a cancer diagnostic application to transmit the acquired cancer diagnosis information to a cancer diagnostic server 30, and displaying cancer diagnosis result information, which is a result of analysis performed by the cancer diagnostic server 30, on a screen.

In this case, as shown in FIG. 2, the cancer diagnostic apparatus 10 includes: a power supply unit 15 for supplying a power; a bio-chip 16 provided at an upper portion thereof with an antibody (captured antibody) reacting with an antigen (ribosomal protein S3; rpS3); an ultraviolet diode 17 for irradiating an ultraviolet ray (UV) from a bottom of the bio-chip 16; a sensor 18 for making an image from a visible ray obtained from the ultraviolet ray, which is converted by the antigen and the antibody bound to each other while passing through the bio-chip 16; a central processing unit (CPU) 19 for extracting only a specific frequency color for a cancer diagnosis from image information outputted from the sensor 18 as a combine ratio coefficient to generate cancer diagnosis information from a pre-set graph of an antibody-and-antigen combine ratio based on the extracted combine ratio coefficient; and a communication unit 19a for converting the cancer diagnosis information generated by the CPU 19 into wireless communication format data to transmit the converted wireless communication format data.

In this case, the user terminal 20 is preferably implemented as a mobile device capable of performing short-range wireless communication with the cancer diagnostic apparatus 10 and capable of performing data communication with the cancer diagnostic server 30 through a network. More preferably, the mobile device is implemented as one of a smart phone, a personal digital assistant (PDA), and a smart pad.

Figure 6:
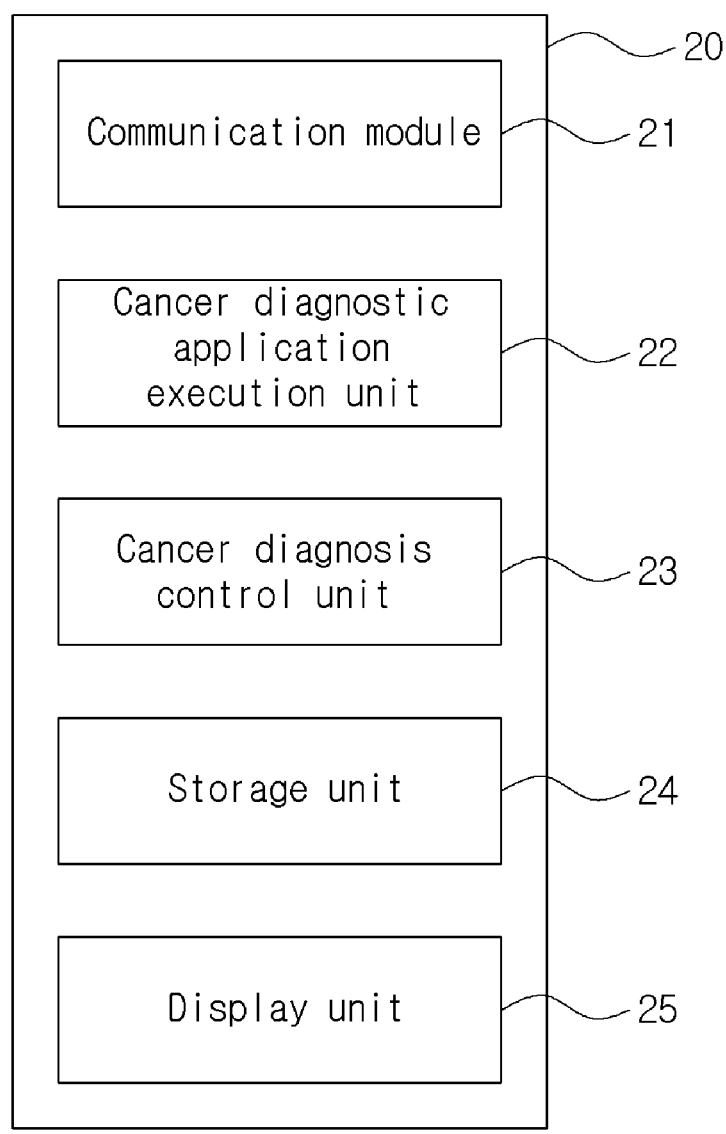
FIG. 6 is a block diagram showing an embodiment of a user terminal of FIG. 5.

In addition, as shown in FIG. 6, the user terminal 20 may include: a communication module 21 for transmitting and receiving cancer diagnosis-related data to and from the cancer diagnostic apparatus 10 and the cancer diagnostic server 30; a cancer diagnostic application execution unit 22 for storing and executing the cancer diagnostic application; a cancer diagnosis control unit 23 for controlling the execution of the cancer diagnostic application, transmitting the cancer diagnosis information received from the cancer diagnostic apparatus 10 to the cancer diagnostic server 30 to request analysis, and controlling storage and display of the cancer diagnosis result information received from the cancer diagnostic server 30; a storage unit 24 for storing the cancer diagnosis result information and cancer diagnosis generation information generated in the cancer diagnosis control unit 23; and a display unit 25 for displaying the cancer diagnosis result information, which is generated from the cancer diagnosis control unit 23, on the screen.

In addition, the cancer diagnostic server 30 preferably diagnoses a cancer incidence by comparing an rpS3 concentration included in the cancer diagnosis information with reference cancer determination data preset based on big data.

Hereinafter, the operation of the cancer diagnostic system using the cancer diagnostic apparatus, which has a configuration as described above, will be described in detail.

First, a process of generating the cancer diagnosis information by using the cancer diagnostic apparatus 10 is identical to a scheme of generating the cancer diagnosis information provided in <Embodiment 1> as described above, reference will be made to <Embodiment 1> for the detailed description in order to avoid duplicate description.

The cancer diagnostic apparatus 10 generates the cancer diagnosis information, converts the generated cancer diagnosis information into short-range wireless communication data, and transmits the short-range wireless communication data to the user terminal 20 as described in <Embodiment 1>.

The user terminal 20 receives the cancer diagnosis information received from the cancer diagnostic apparatus 10 through the communication module 21, and stores the received cancer diagnosis information in the storage unit 24.

Next, to perform the cancer diagnosis, the cancer diagnosis control unit 23 of the user terminal 10 controls the cancer diagnostic application execution unit 22 to execute the cancer diagnostic application. When the cancer diagnostic application is executed, the cancer diagnosis control unit 23 is connected to the cancer diagnostic server 30 by the communication module 21 through the network according to the cancer diagnostic application. When the connection is established, the cancer diagnosis information stored in the storage unit 24 is transmitted to the cancer diagnostic server 30, and the analysis is requested.

The cancer diagnostic server 30 which received a request for the analysis analyzes the cancer incidence by comparing the rpS3 concentration included in the cancer diagnosis information with the reference cancer determination data preset based on cancer diagnosis information acquired as the big data.

Figure 7:
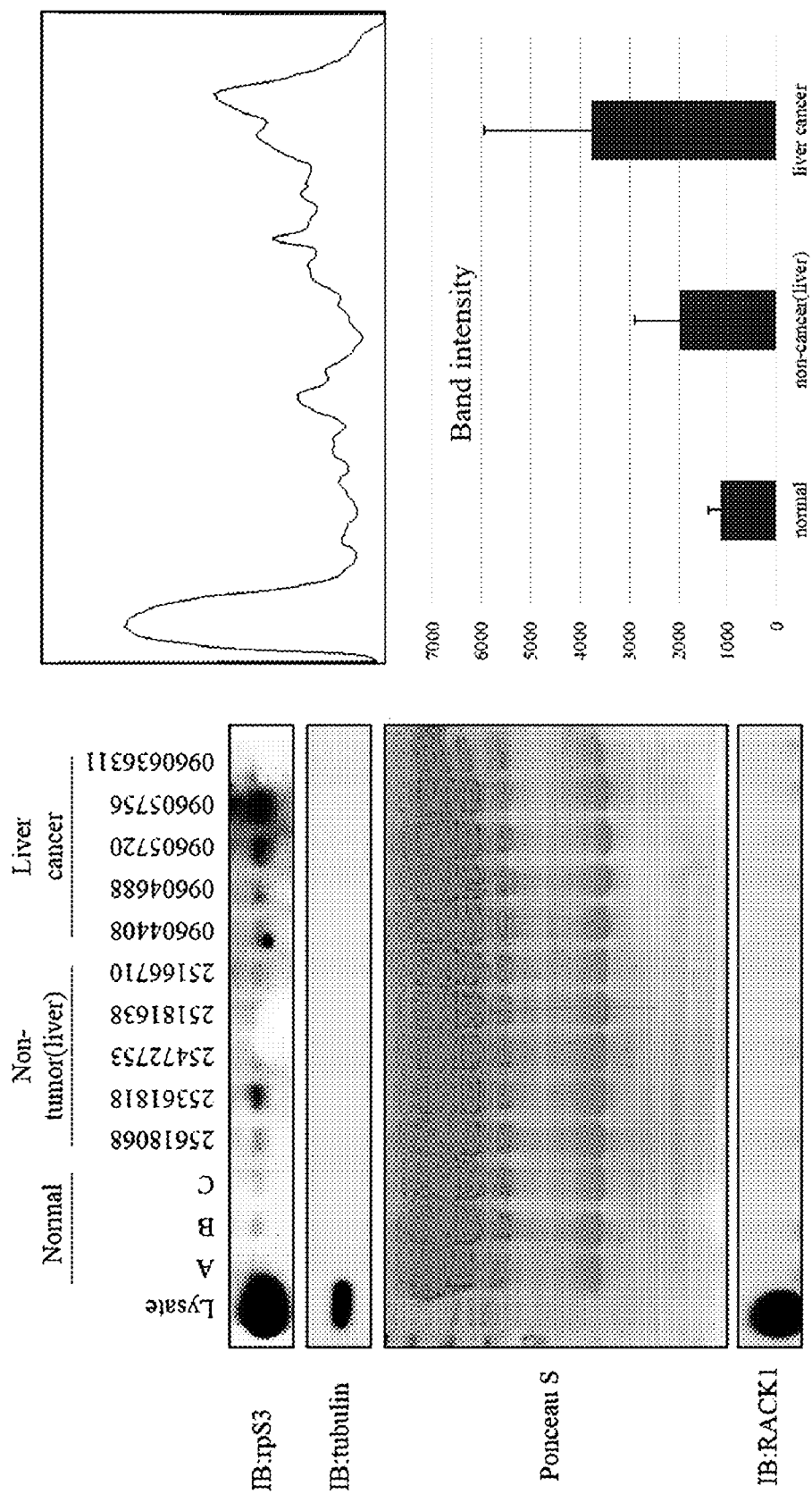
FIGS. 7 and 8 are conceptual views for explaining calculation of reference cancer determination data based on big data according to the present invention.
Figure 8:
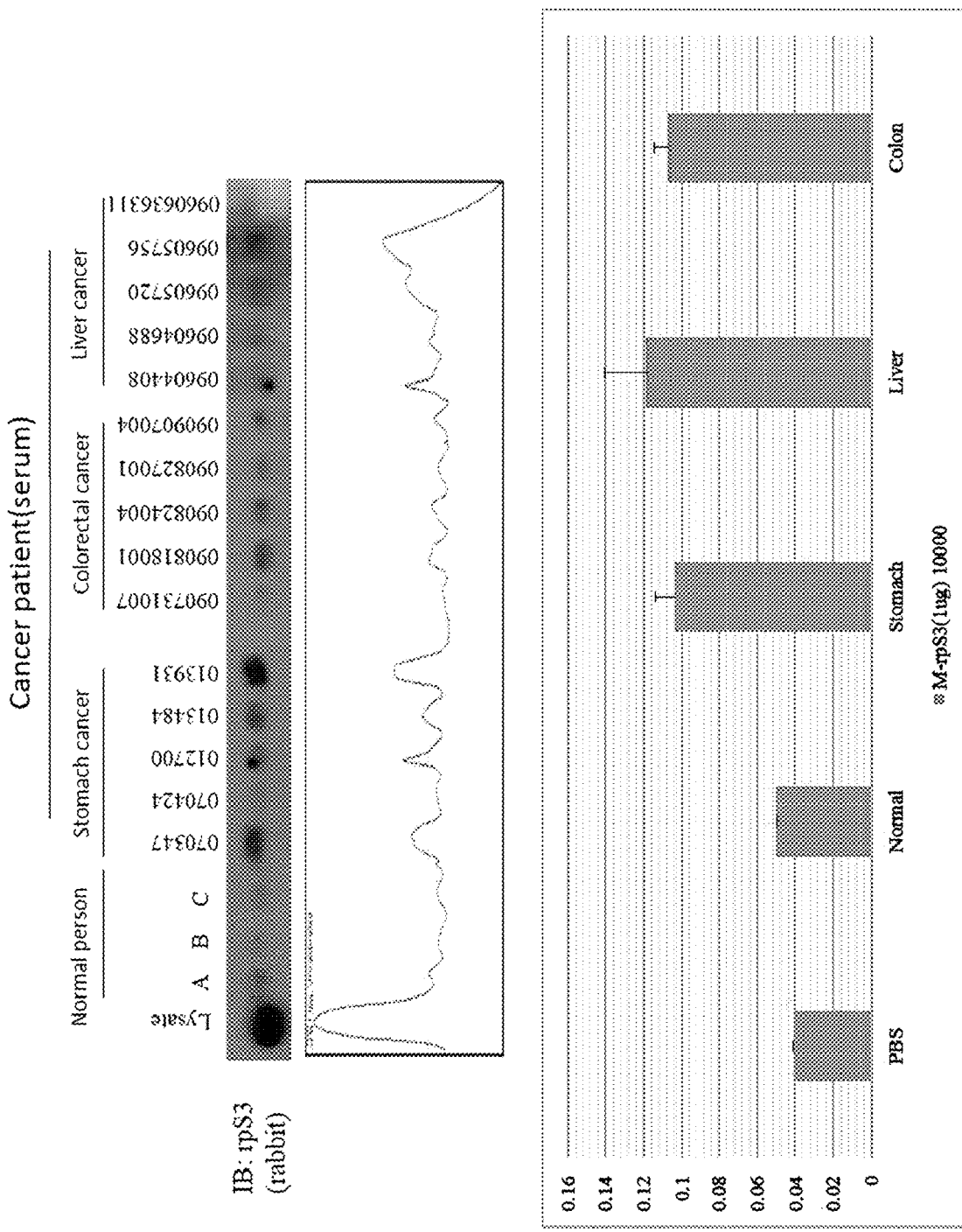

For example, the cancer diagnostic server 30 acquires a plurality of pieces of cancer diagnosis information as the big data and analyzes the acquired cancer diagnosis information to set the reference cancer determination data as shown in FIGS. 7 and 8.

Figure 9:
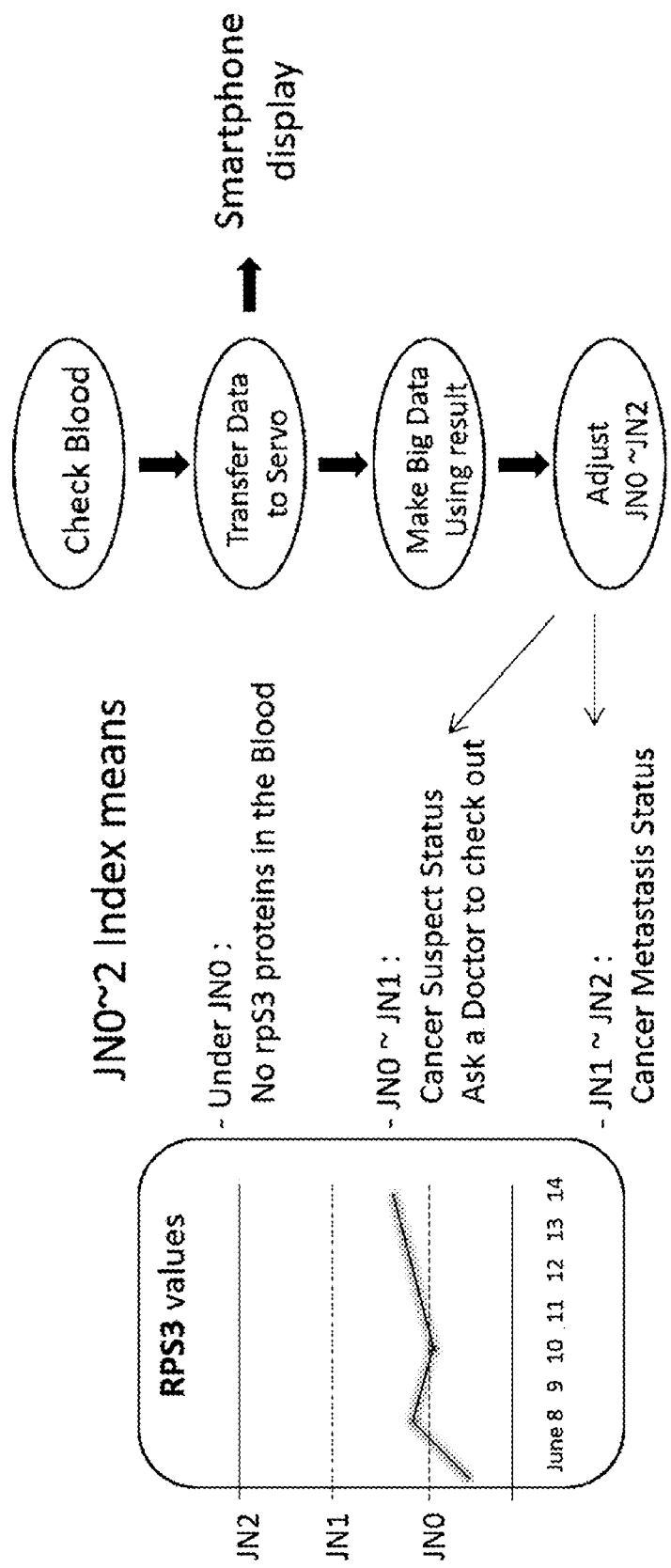
FIG. 9 is a view illustrating a cancer diagnosis result.

In addition, the rpS3 concentration included in the cancer diagnosis information received from the user terminal 20 is compared and analyzed based on the reference cancer determination data to finally generate the cancer diagnosis result information. The generated cancer diagnosis result information is shown in FIG. 9.

In the cancer diagnosis result information, a value (concentration) of the rpS3 which is determined to be JN2 indicates the cancer diagnosis result information without the rpS3 in the blood. In addition, JN1 to JN2 indicate a cancer metastasis state, and IN0 to JN1 indicate a cancer suspicion state so that the user should visit a doctor for a thorough medical examination.

The cancer diagnosis result information is transmitted to the user terminal 20 through the network.

The cancer diagnosis control unit 23 of the user terminal 20 receives the cancer diagnosis result information and stores the cancer diagnosis result information in the storage unit 24, and displays the cancer diagnosis result information on the screen through the display unit 25.

Figure 10:
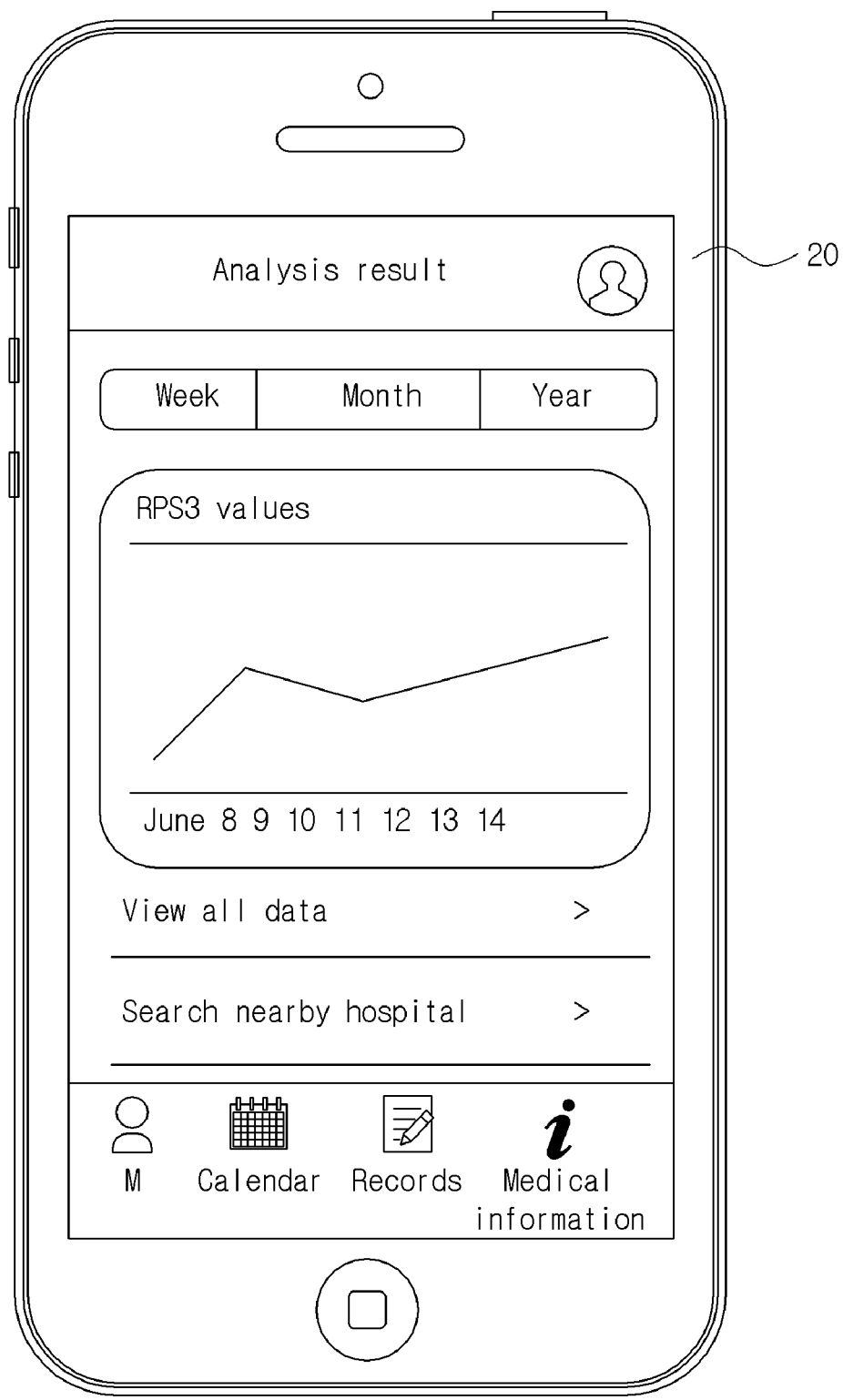
FIG. 10 is a view illustrating a screen for displaying the cancer diagnosis result in the user terminal.

FIG. 10 shows an example of displaying the cancer diagnosis result information on the screen.

Therefore, the user can diagnose the cancer in real time through the cancer diagnosis result information displayed on the screen as described above, and the thorough medical examination is performed in the hospital when the cancer is suspected based on the cancer diagnosis result information displayed on the screen.

As described above, since the cancer diagnosis can be simply performed in real time by using only the cancer diagnostic apparatus and the user terminal, the general user who does not have the medical expertise can arbitrarily diagnose the cancer at any time before the thorough medical examination in the hospital, so that there is an excellent effect of making sure of good health by checking a health condition at all times.

Although the present invention invented by the present inventor has been described in detail with reference to the embodiments, the present invention is not limited to the above embodiments, and it is to be understood to those skilled in the art that various modifications are possible without departing from the scope and spirit of the present invention.

The present invention is applied to a technique for allowing a general user who does not have medical expertise to self-diagnose a cancer.

What is claimed is:

1. A cancer diagnostic system using a cancer diagnostic apparatus, the cancer diagnostic system comprising:
the cancer diagnostic apparatus for irradiating an ultraviolet ray (UV) from a bottom of a bio-chip provided with an antibody reacting with an antigen ribosomal protein S3 (rpS3), making an image from a visible ray obtained from the ultraviolet ray, which is converted by the antigen and the antibody bound to each other while passing through the bio-chip, and extracting only a specific frequency color from the visible ray to generate cancer diagnosis information; and
a user terminal for acquiring the cancer diagnosis information generated by the cancer diagnostic apparatus through a cancer diagnostic application to transmit the acquired cancer diagnosis information to a cancer diagnostic server, and displaying cancer diagnosis result information, which is a result of analysis performed by the cancer diagnostic server, on a screen,
wherein the cancer diagnostic apparatus includes:
a power supply unit for supplying a power;
a bio-chip provided at an upper portion thereof with the antibody reacting with the antigen (ribosomal protein S3; rpS3);
an ultraviolet diode for irradiating the ultraviolet ray (UV) from the bottom of the bio-chip;
a sensor for making the image from the visible ray obtained from the ultraviolet ray, which is converted by the antigen and the antibody bound to each other while passing through the bio-chip;
a central processing unit (CPU) for extracting only the specific frequency color for a cancer diagnosis from image information outputted from the sensor as a combine ratio coefficient to generate the cancer diagnosis information from a pre-set graph of an antibody-and-antigen combine ratio based on the extracted combine ratio coefficient; and
a communication unit for converting the cancer diagnosis information generated by the CPU into wireless communication format data to transmit the converted wireless communication format data,
wherein the combine ratio coefficient refers to the coefficient at a specific time of the hyperbolic function that represents the combine ratio of the antigen and antibody when combined in a specific amount.

2. The cancer diagnostic system of claim 1, wherein the sensor includes:
   a camera lens for focusing the visible ray obtained from the ultraviolet ray, which is irradiated upward from the bottom of the bio-chip and converted by the antigen and the antibody bound to each other while passing through the bio-chip, to photograph the visible ray; and
   an image sensor for photographing the visible ray focused by the camera lens to make the image.

3. The cancer diagnostic system of claim 1, wherein the CPU compares the combine ratio coefficient with the pre-set graph of the antibody-and-antigen combine ratio to generate the cancer diagnosis information after the antibody and the antigen are completely bound to each other.

4. The cancer diagnostic system of claim 1, wherein the user terminal is implemented as a mobile device capable of performing short-range wireless communication with the cancer diagnostic apparatus and capable of performing data communication with the cancer diagnostic server through a network, and
   the mobile device is one of a smart phone, and a personal digital assistant (PDA).

5. The cancer diagnostic system of claim 1, wherein the user terminal includes:
   a communication module for transmitting and receiving cancer diagnosis-related data to and from the cancer diagnostic apparatus and the cancer diagnostic server;
   a cancer diagnostic application execution unit for storing and executing the cancer diagnostic application;
   a cancer diagnosis control unit for controlling the execution of the cancer diagnostic application, transmitting the cancer diagnosis information received from the cancer diagnostic apparatus to the cancer diagnostic server to request analysis, and controlling storage and display of the cancer diagnosis result information received from the cancer diagnostic server; and
   a display unit for displaying the cancer diagnosis result information, which is generated from the cancer diagnosis control unit, on the screen.

6. The cancer diagnostic system of claim 1, wherein the cancer diagnostic server diagnoses a cancer incidence by comparing an rpS3 concentration included in the cancer diagnosis information with reference to preset cancer determination data.

* * * * *